US008871682B2

(12) United States Patent
Podella et al.

(10) Patent No.: US 8,871,682 B2
(45) Date of Patent: *Oct. 28, 2014

(54) PROTEIN COMPOSITIONS FOR PLANT TREATMENT

(75) Inventors: Carl W. Podella, Irvine, CA (US); Jack W. Baldridge, Newport Beach, CA (US); Andrew H. Michalow, Mission Viejo, CA (US); Michael G. Goldfeld, Irvine, CA (US)

(73) Assignee: Advanced Biocatalytics Corporation, Irvine, CA (US)

( * ) Notice: Subject to any disclaimer, the term of this patent is extended or adjusted under 35 U.S.C. 154(b) by 21 days.

This patent is subject to a terminal disclaimer.

(21) Appl. No.: 13/140,830

(22) PCT Filed: Dec. 11, 2009

(86) PCT No.: PCT/US2009/067779
§ 371 (c)(1),
(2), (4) Date: Feb. 14, 2012

(87) PCT Pub. No.: WO2010/068932
PCT Pub. Date: Jun. 17, 2010

(65) Prior Publication Data
US 2012/0142530 A1 Jun. 7, 2012

Related U.S. Application Data

(60) Provisional application No. 61/201,661, filed on Dec. 12, 2008, provisional application No. 61/201,600, filed on Dec. 12, 2008.

(51) Int. Cl.
*A01N 37/46* (2006.01)
*A01P 21/00* (2006.01)
*C05F 11/10* (2006.01)
*C05G 3/06* (2006.01)

(52) U.S. Cl.
CPC .. *C05F 11/10* (2013.01); *C05G 3/06* (2013.01)
USPC .......................................... 504/117; 504/335

(58) Field of Classification Search
USPC ............................................................ 71/26
See application file for complete search history.

(56) References Cited

U.S. PATENT DOCUMENTS

| | | | |
|---|---|---|---|
| 3,561,944 A * | 2/1971 | Battistoni et al. | ................. 71/26 |
| 6,699,391 B2 | 3/2004 | Baldridge | |
| 7,165,561 B2 | 1/2007 | Baldridge | |
| 7,476,529 B2 | 1/2009 | Podella | |
| 7,645,730 B2 | 1/2010 | Baldridge | |
| 7,658,848 B2 | 2/2010 | Baldridge | |
| 7,659,237 B2 | 2/2010 | Baldridge | |
| 7,759,301 B2 | 7/2010 | Baldridge | |
| 7,922,906 B2 | 4/2011 | Baldridge | |
| 2004/0180411 A1 | 9/2004 | Podella | |
| 2006/0201877 A1 | 9/2006 | Baldridge | |
| 2007/0131010 A1* | 6/2007 | Binder et al. | ..................... 71/23 |
| 2008/0167445 A1 | 7/2008 | Podella | |
| 2008/0269053 A1 | 10/2008 | Less | |
| 2009/0152196 A1 | 6/2009 | Podella | |
| 2010/0099599 A1 | 4/2010 | Michalow | |

FOREIGN PATENT DOCUMENTS

| | | |
|---|---|---|
| AU | 776176 B2 | 2/2001 |
| EP | 0940380 A1 | 9/1999 |
| WO | 2004/071195 A1 | 8/2004 |
| WO | 2010/091433 A1 | 8/2010 |

OTHER PUBLICATIONS

Pérez-Torrado, R. et al. "Monitoring Stress-Related Genes during the process of Biomass propagation of *Saccharomyces cerevisiae* strains used for wine making." Applied and Environmental Microbiology, 2005, 71, 6831-6837.*
Kulkarni et al., "Evaluating variability of root size system and its constitutive traits in hot pepper (*Capsicum annum* L.) under water stress," Scientia Horticulturae 120 (2009) 159-166.
Li et al., "Root and shoot traits responses to phosphorous deficiency and QTL analysis at seedling stage using introgression lines of rise," J. Genet. Genomics 36 (2009) 173-183.
Aikio et al., "Dynamics of biomass partitioning in two competing meadow plant species," Plant Ecol (2009) 205:129-137.
Aikio et al., "Optimality and phenotypic plasticity of shoot-to-root ratio under variable light and nutrient availabilities," Evolutionary Ecology 16:67-76, 2002.
Snyman, "Root studies on grass species in a semi-arid South Africa along a degradation gradient," Agriculture, Ecosystems and Environment 130 (2009) 100-108.
Tchienkoua et al., "Biomass and Phosphorous Uptake Responses of Maize in Phosphorous Application in Three Acid Soils from Southern Cameroon," Communications in Soil Science and Plant Analysis, 39:1546-1558, 2008.
Zhang et al., "Root size, distribution and soil water depletion as affected by cultivars and environmental factors," Field Crops Research 114 (2009) 75-83.

* cited by examiner

Primary Examiner — Mina Haghighatian
Assistant Examiner — Erin Hirt
(74) Attorney, Agent, or Firm — Sam K. Tahmassebi; TechLaw LLP

(57) ABSTRACT

Disclosed herein are methods of accelerating root growth in a plant, the method comprising applying to the plant root a composition comprising a) a mixture of proteins and polypeptides, and b) a surfactant, whereby root growth is accelerated as compared to an untreated plant. Also disclosed herein are methods of improving the foliar uptake of a biologically active compound by a plant, the method comprising applying to the plant foliage a composition comprising a) a mixture of proteins and polypeptides, and b) a surfactant, whereby root growth is accelerated as compared to an untreated plant.

10 Claims, No Drawings

PROTEIN COMPOSITIONS FOR PLANT TREATMENT

RELATED APPLICATIONS

This application is filed under 35 U.S.C. §371 as the U.S. national phase of International Application PCT/US2009/067779, filed Dec. 11, 2009, which designated the U.S. and claims priority to the U.S. Provisional Application Ser. No. 61/201,600, filed on Dec. 12, 2008, by Michalow, et al., and entitled "PROTEIN COMPOSITIONS THAT IMPROVE SOIL PENETRATION AND ROOT UPTAKE OF WATER AND NUTRIENTS", and to the U.S. Provisional Application Ser. No. 61/201,661, filed on Dec. 12, 2008, by Podella, et al., and entitled "PROTEIN ENHANCED PLANT TREATMENT ADJUVANT COMPOSITIONS", the entire disclosure of both of which is incorporated by reference herein.

FIELD OF THE INVENTION

The invention belongs to the field of agricultural chemicals, more specifically to the materials which improve the transfer to, penetration into, and uptake by the foliage and roots of agricultural plants of water and water-soluble chemicals, or herbicides by the shoots or roots of weeds. The invention also relates to the field of adjuvants used to increase the foliar uptake of biologically active compounds.

BACKGROUND OF THE DISCLOSURE

The dimensions of root systems vary dramatically between plant species, and differ within the same species depending on soil/growth conditions. Roots provide the key mechanism of uptake of water and nutrients for plants by developing a complex network structure within soil. They maintain a symbiotic relationship with microbes by secreting compounds that feed microbes, which then break down organic nutrients into forms that can be more readily absorbed by the roots and utilized by the plant. The robustness of the root system is a key factor to the yield that a plant can produce. It is desirable to have a more dense root system, as increased in root density translates into a faster growth for the plant, which is agriculturally and economically useful.

Further, many biologically active compounds, such as pesticides, are sprayed on the leaves of plants for foliar uptake. Plant leaves are generally waxy with small pores, which make it difficult for the organic molecules to penetrate the leaf. Solutions containing the active compounds typically contain adjuvants that help with the foliar uptake. However, the adjuvants currently used are not very efficient and most of the biologically active compounds do not reach their targets.

SUMMARY OF THE INVENTION

Disclosed herein are methods of accelerating root growth in a plant, the method comprising applying to the plant root a composition comprising a) a mixture of proteins and polypeptides, and b) a surfactant, whereby root growth is accelerated as compared to an untreated plant. Also disclosed herein are methods of improving the foliar uptake of a biologically active compound by a plant, the method comprising applying to the plant foliage a composition comprising a) a mixture of proteins and polypeptides, and b) a surfactant, whereby root growth is accelerated as compared to an untreated plant.

DETAILED DESCRIPTION OF THE EMBODIMENTS

Most plant absorption is believed to take place in the fine roots, less than two millimeters in diameter, and root hair at the tip of the root, forming big surface area. For roots to be able to uptake nutrients or other chemicals, they must come into contact with those chemicals. To "feed" the roots, it is therefore essential that the mass flow of water, macro- and micro-nutrients, herbicides, various growth treatments, collectively to be called "effector," is directed toward the immediate vicinity of the roots. Then diffusion driven by the concentration gradients results in uptaking the effector by the root.

In most cases, such as turf, agriculture, ornamentals, etc., where harvesting is a goal, it is important to develop adequately large root systems and as quickly as possible to optimize yield within a growing period. In plug propagation root maturity can range from three weeks for *Colesia* species to ten weeks for *Ranunculus*, to over fourteen weeks for *Cyclamen*. Faster root growth reduces time to maturity when plants are ready for transplant, which can cut costs substantially at plug nurseries. In some species of plants, the initial shoot growth far outpaces root growth, which makes transplanting more difficult and may require use of shoot growth inhibitors. Many herbs such as tarragon, oregano and savory have a difficult time developing good root systems. In agricultural production of tarragon, for example, the root systems are typically thin and delicate. Abrupt changes in environmental conditions can be detrimental to a crop reducing yields by 70% in some cases. Tarragon can be harvested numerous times from a single plant, being cut back multiple times.

Plant's growth cycle after seeding typically starts with a foundation of a tap root that extends down with side branching following. At some point of root maturity, the embryonic first leaves penetrate through the soil of the seedling, the cotyledon stage. It has been observed that the protein-surfactant complexes (PSC) disclosed herein stimulate root growth once roots start to appear, and at this early growth stage appears to focus the plant's energy production toward root growth, which takes away somewhat from shoot growth. At a certain point in root maturity the more dense roots then have the capacity to accelerate shoot growth relative to root density for a particular plant species, as would be expected with more dense root systems.

In plug nurseries, the goal is to allow the plants to mature to a point where the roots can be easily transplanted. This is done by pulling plugs to determine whether the entire root mass and soil remain intact when pulled. In some plant species the shoots grow disproportionately fast as compared to the roots, which means that the plants could be fragile when transplanting. In such species, plant growth regulators are used to reduce the shoot growth rate at early stages of plant growth. One of the features of the PSCs disclosed herein is that they show the ability in early stages of a plant's growth cycle to enhance the root growth, while at the same time curtailing the shoot growth. This provides many benefits for a nursery. The application of a plant growth regulator (PGR) for species such as Vinca vine, is typically done manually. Both the cost of the PGR and the labor for application are significant. The second disadvantage for growers is that the PGR has to be applied before the excess shoot growth. The PSC, on the other hand can be fed at a low dose continuously with each watering cycle, including nutrients as needed. The cost of the PSC is relatively low and there is no secondary, manual dosing application required.

PGRs are generally plant hormones, chemicals that regulate plant growth in various aspects. They are produced within plants and occur in extremely low concentrations, $10^{-5}$ to $10^{-6}$ mol/L There are several classes of PGRs: abscisic acid, auxins, cytokinins, ethylene generators, gibberellins, brassinolides. The PSC does not fall under any of these classes. PGRs are typically dosed in limited applications at a very specific period of a plant's growth cycle to elicit a desired response. For example, auxins are used to promote root growth by dipping cuttings into an auxin based solution in one step. PGRs in general can be phytotoxic in higher concentrations.

PGRs are well known and regularly used in agriculture. The purpose of a PGR is to manipulate the growth rate of a plant to accelerate or inhibit certain aspects of plant growth—roots, shoots, vegetation, sprouting, ripening, side branching, canopy, etc. Many agents are synthetic chemicals.

The PSC effects as a plant growth regulator have been limited in growth effects. In early stages of plug propagation, it was observed that plants accelerated root growth at the expense of shoot growth. This was not observed in all species, but is likely due to different growth cycles. The heights of Vinca, broccoli, *Gerbera* Daisies, Tarragon were reduced, while root production was either enhanced or the same as controls. All of the species were treated with, more or less, continuous dosing with water cycles.

From a safety and environmental perspective, a key difference between the PSC and other PGR's, drip line treatments, adjuvants systems and agricultural chemical treatments is that the PSC is classified as a "food" when appropriate surfactants, like sodium lauryl sulfate, Sorbitans and other food additive surfactants are used. The PSC is environmentally and toxicologically benign, again, when appropriate surfactants are used. A range of such surfactants exist that can be chosen from to optimize performance for a particular set of conditions and desired effects. From a regulatory standpoint, this means that the PSCs disclosed herein have minimal regulatory hurdles. As an example to distinguish the safety benefits of the PSC, if typical PGR's were accidentally misapplied, environment effects could be detrimental. The PSC can be applied at a minimum concentration of 12 ppm and with, more or less, continuous dosing the PSC's can accumulate in the short-term when root systems are constrained, as in pot growth.

Further, the protein component has been shown to be environmentally benign. Using OECD (Office of Environmental Compliance and Documentation) Method 301B ($CO_2$ Evolution Test) the proteins were shown to be "readily biodegradable" according to Group of Experts on Scientific Aspects of Marine Environmental Protection (GESAMP) Hazard Evaluation procedure and was not inhibitory to the degradation of the reference compound, which is the surfactant component. In aquatic toxicity analysis, at up to 10,000 ppm (1%) of the proteins, survival of sheepshead minnow was 100%. The tests followed protocol and guidelines followed by the U.S. Environmental Protection Agency (USEPA) Ecological Effects Tests Guidelines (OECD Guideline for Testing Of Chemicals 203), supplemented by the USEPA Acute guidelines for Whole Effluent Toxicity testing. Finally, the GESAMP hazard profile rating was concluded to be zero and that the hydrophilic proteins are "estimated to have no potential to bioaccumulate based on the GESAMP hazard profile rating scheme (Section 4.1.1.2, Table 3 of GESAMP Procedure Document). Accidental spillage or misapplication of the PSC should not cause any harm either to the environment or to a grower or the grower's crops.

Accidental spillage or misapplication of the PSC should not cause any harm either to the environment or to a grower or the grower's crops.

In a growth area with adequate weather, where watering and feeding are not limiting factors in root development, the soil/growth media conditions become the determining factor in how well roots, and then the desired plant features, will grow. Growth media, in addition to soil, can range from porous ceramics materials, to highly organic composts and peat, clay pebbles, vermiculite, coconut fibers, perlite and others. The purpose of soil or any growth media is to support the plant roots, retain moisture, allow space for good air flow for oxygen to get to the roots and act as a nutrient delivery system.

Most agriculture is grown, however in some type of soil. Soil conditions are characterized by a number of features including its bulk density, porosity, pore size, aggregate structure and soil chemistry. For example, soil particles can be hydrophobic (lipophilic), or water resistant, and this condition reduces water permeability into the soil and reduces water retention by preventing wetting of soil particles. Consistent wetting of soil promotes dense root growth and is necessary for healthy root growth. The PSC compositions of the current invention improve wetting of soil and penetration of aqueous solutions into soils.

A key benefit to the embodiments of the current invention is that water usage can be significantly reduced both directly through improved soil/growth media penetration and retention, and indirectly by improving productive yield. Worldwide, agriculture is responsible for 70% of water use by humans and fresh water resources are diminishing in many areas. Though 60% of food is produced using rain-fed systems, supplemental irrigation can increase yields substantially.

One of the most efficient ways to deliver water and aqueous compounds to plants is the use of drip irrigation systems. Drip systems can, for example, improve banana yields by 52% with 45% less water. But drip systems are prone to plugging from particles in water, scaling or biofouling in the form of biofilms, or their combination. Biofilms are particularly problematic as they exacerbate the scaling problem and act to trap particulates both of which enhance the plugging tendency. The PSC does not exhibit direct scale inhibiting characteristics and it is surmised, though not a limitation to the current invention, that the biofilm control mechanism is helping to achieve scale inhibition, where the formation of a biofilm acts as a propagation site and forms a composite structure with the scale-causing molecules.

In a field study with water typically above 1,000 ppm total dissolved solids, a good portion of which is calcium and magnesium hardness, and iron, a PSC content of under 10 ppm would not control scale if it was directly interacting with scale-causing molecular species. A 1 ppm dose was used to control scale. The low dose rate adds to benign nature of the PSC for scale and fouling control and, further, reduces costs, which makes its use practical and cost effective in both low value and high value plant species. To control drip irrigation. To control drip irrigation line and nozzle tip plugging, filtering techniques, and chemical cleaners and treatments have traditionally been used.

Chlorination is one method to control biological growth, but chlorine is environmentally hazardous and forms chloramines with ammonia in effluents used in irrigation. Chloramines are 80 times less effective than chlorine in controlling biological growth. Further, the PSC is generally non-reactive with nutrients, such as N, P, K, etc., and in this regard can be fed in conjunction with the nutrients. This would simplify the dosing process by eliminating a second operation to add cleaning chemicals to a drip system.

In some instances copper salts have been used with the dual purpose of being antimicrobial agents to control bacterial growth in drip irrigation lines, and then act as micronutrients once in the soil. However, copper salts can be toxic and pose risks to farm workers. In addition, the copper solution would have to be continuously dosed to prevent biofilm formation. Once biofilms form, the copper would not be able to penetrate or remove them. Other cleaning systems use phosphonic acids and organic phosphonic acids or fatty acids to clean lines. These are typically below pH of 2 to clean lines and then the phosphorus acts as nutrient in the soil. The low pH can be hazardous to the farm worker and equipment. Continuous feed to maintain clean lines could be costly and overfeeding of phosphorus could lead to run-off of phosphorus, which can exacerbate eutrophication of ecosystems. Many of these need to be metered in and this adds to the workload of the farm worker. In the current invention the PSC composition is designed to be supplied continuously, intermittently, typically between 1 to 10 ppm, simplifying application and keeping costs low.

As discussed herein below, the protein enhanced surfactants can be effective in both foliar and root uptake. This could simplify the end users' needs when it comes to inventory of adjuvants and when foliar application is used, the overspray is not wasted but has efficacy in soil or other growth media treatment.

Root Growth Applications

The prototype formulae consist of two primary components;

1) surfactants that facilitate the penetration of the water into the soil or other growth media, and increase bioavailability to the plant's roots, and 2) proteins derived from the yeast fermentation, which increase the functionality of the surfactants by further reducing the interfacial tension of the surfactant solution, and reducing the critical micelle concentration of the surfactant, thus allowing a reduction in the amount of surfactant required to achieve good penetration of the water.

Surfactants

Surfactants that are useful in the protein/surfactant complex may be either nonionic, anionic, amphoteric or cationic, or a combination of any of the above, depending on the aqueous filtration application. Suitable nonionic surfactants include alkanolamides, amine oxides, block polymers, ethoxylated primary and secondary alcohols, ethoxylated alkylphenols, ethoxylated fatty esters, sorbitan derivatives, glycerol esters, propoxylated and ethoxylated fatty acids, alcohols, and alkyl phenols, glycol esters, polymeric polysaccharides, sulfates and sulfonates of ethoxylated alkylphenols, and polymeric surfactants. Suitable anionic surfactants include ethoxylated amines and/or amides, sulfosuccinates and derivatives, sulfates of ethoxylated alcohols, sulfates of alcohols, sulfonates and sulfonic acid derivatives, phosphate esters, and polymeric surfactants. Suitable amphoteric surfactants include betaine derivatives. Suitable cationic surfactants include amine surfactants. Those skilled in the art will recognize that other and further surfactants are potentially useful in the PSC composition. Some examples of surfactants that may be applicable for use in the soil penetration and root uptake compositions described herein include the following:

Anionic: Sodium linear alkylbenzene sulfonate (LABS); sodium lauryl sulfate; sodium lauryl ether sulfates; sodium dioctyl sulfosuccinates; petroleum sulfonates; linosulfonates; naphthalene sulfonates; branched alkylbenzene sulfonates; linear alkylbenzene sulfonates; fatty acid alkylolamide sulfosuccinate; alcohol sulfates.

Cationic: Stearalkonium chloride; ammonium compounds, such as benzalkonium chloride; quaternary ammonium compounds; amine compounds; ethosulfate compounds.

Non-ionic: Dodecyl dimethylamine oxide; coco diethanolamide alcohol ethoxylates; linear primary alcohol polyethoxylate; alkyl phenol ethoxylates; alcohol ethoxylates; EO/PO polyol block polymers; polyethylene glycol esters; fatty acid alkanolamides.

Amphoteric: Cocoamphocarboxyglycinate; cocamidopropyl betaine; betaine derivatives; imidazoline derivatives.

Several of the known surfactants are non-petroleum based. For example, several surfactants are derived from naturally occurring sources, such as vegetable sources (coconuts, palm, castor beans, etc.). These naturally derived surfactants may offer additional benefits such as biodegradability.

It should be understood that these surfactants and the surfactant classes described above are identified only as preferred materials and that this list is neither exclusive nor limiting of the compositions and methods described herein.

Fermentation

There have been numerous attempts in the past to utilize chemicals from fermentation of yeast. The current patent is differentiated from these in subtle, yet critical and relevant, ways. Fermentation of yeast is used for applications including the production of beer, sake and enzymes. The specifics of the present invention's fermentation process form the basis for its uniqueness and divergence from these other processes. These have been discussed in previous patent applications (See U.S. Pat. Appn. Nos. 20050245414, 20040180411 and 20080167445, all of which are incorporated herein by reference in their entirety).

The present inventor obtained low molecular weight protein factor from yeast fermentation, preferably aerobic, processes which, when coupled with surfactants, reduce the critical micelle concentration of surfactants, surface tension and interfacial tension of surfactant solutions, with reductions in the critical micelle concentration, surface tension, and interfacial tension as compared to the surfactants taken alone, and further reduction of the same parameters observed after exposure to grease and oil. This factor was found in the yeast fermentation-derived polypeptide fractions ranging in molecular weights between about 6,000 and 17,000 daltons by the results of polyacrylamide gel electrophoresis.

The compositions disclosed herein comprise a yeast aerobic fermentation supernatant, surface-active agents and stabilizing agents. *Saccharomyces cerevisiae* is grown under aerobic conditions familiar to those skilled in the art, using a sugar source, such as molasses, or soybean, or corn, or cane sugar, as the primary nutrient source. Alternative types of yeast that can be utilized in the fermentation process may include: *Kluyveromyces maxianus, Kluyeromyces lactus, Candida utilis* (Torula yeast), *Zygosaccharomyces, Pichia* and *Hansanula*. Those skilled in the art will recognize that other and further yeast strains are potentially useful in the fermentation and production of the low molecular weight proteins, "the protein system." It should be understood that these yeasts and the yeast classes described above are identified only as preferred materials and that this list is neither exclusive nor limiting of the compositions and methods described herein.

The proteins of the disclosed compositions comprise proteins, protein fragments, peptides, and stress proteins having a size less than 30 kDa. In some embodiments, the size range is from about 0.5 kDa to about 30 kDa. Throughout the present disclosure, the protein mixture used in the PSC compositions disclosed herein is referred to as the "protein system."

The word "peptide" includes long chain polypeptides, such as proteins, as well as short chain peptides, such as dimers, trimers, oligomers, and protein fragments. In some embodiments, the words "polypeptide" and "protein" are interchangeable.

In some embodiments, the protein systems disclosed herein are derived from a fermentation of *Saccharomyces cerevisiae*, which, when blended with surface active agents or surfactants, enhance multiple chemical functions. The protein systems disclosed herein can also be derived from the fermentation of other yeast species, for example, *kluyveromyces marxianus, kluyveromyces lactis, candida utilis, zygosaccharomyces, pichia,* or *hansanula*. In a preferred embodiment, the fermentation process is aerobic.

After the aerobic fermentation process, a fermentation mixture is obtained, which comprises the fermented yeast cells and the proteins and peptides secreted therefrom. In some embodiments, the fermentation mixture can be subjected to additional stress, such as overheating, starvation, overfeeding, oxidative stress, or mechanical or chemical stress, to obtain a post-fermentation mixture. The additional stress causes additional proteins ("stress proteins") to be expressed by the yeast cells and released into the fermentation mixture. These additional proteins are not normally present in significant quantity during a simple fermentation process. Once the post-fermentation mixture is centrifuged, the resulting supernatant comprises both the stress proteins and proteins normally obtained during fermentation. The post-fermentation mixture may then be stabilized to prevent degradation or bacterial contamination through the use of antimicrobial agents, preservatives and/or pH adjustment. The compositions described herein comprise stress proteins.

The preferred embodiments of fermentation processes used for the current invention are defined in previous patent applications (See U.S. Pat. Appn. Nos. 20050245414, 20040180411 and 20080167445, all of which are incorporated herein by reference in their entirety). In addition, the ratio of fermentation supernatant to surfactant is optimally in the range of 1 to 3, but in instances where emulsifying characteristics are not important, it has been found that interfacial tension can be reduced with higher protein (supernatant) ratio relative to the amount of surfactant. Alternatively, the protein ratio might be much less than 1. The broad range of functionality gives the formulator flexibility in optimizing products for specific end uses because the range of different types of biologically active compounds (BAC's) may be more or less compatible with the protein based adjuvant.

The application of stress proteins to improve the performance of surface active agents has been previously introduced in other fields by the Assignee of the current invention and these were limited to application on inanimate surfaces. It was well documented in the previous patents and patent applications that yeast proteins considerably enhance surface activity of a broad range of synthetic detergents, reducing surface and interfacial tension, dynamic surface tension, interfacial tension and critical micelle concentration in their solutions, and enhance their performance in such areas as control and prevention of biofilm formation, waste water treatment, cleaning, soil remediation, odor control, etc. These fundamental aspects are now applied in the current invention for application in the field of agricultural chemicals, or adjuvants for active biological compounds.

Plant Growth Tests:

Treatments included a fermentation-based protein system, two surfactant systems, and combinations thereof and an untreated control (fertilizer only). The Examples are describes as follows:

Example 1

A fermentation mixture that is derived from the fermentation of *Saccharomyces cerevisiae* in which the yeast cells are stressed by raising the temperature to at least 35° C. for at least two hours, then cooling to <30° C. prior to centrifugation. Upon removal of the yeast cells by centrifugation, the pH is adjusted to 4.0 and, 0.42% sodium benzoate and 21.10% propylene glycol is incorporated to provide stability.

| Component | Composition (%) by Weight |
| --- | --- |
| Stabilized Fermentation Mixture | 70.00% |
| Water | 30.00% |
| Total | 100.00% |

Example 2

A fermentation mixture that is derived from the fermentation of *Saccharomyces cerevisiae* in which the yeast cells are stressed by raising the temperature to at least 35° C. for at least two hours, then cooling to <30° C. prior to centrifugation. Upon removal of the yeast cells by centrifugation, the pH is adjusted to 4.0 and 0.42% sodium benzoate is incorporated to provide stability.

| Component | Composition (%) by Weight |
| --- | --- |
| Stabilized Fermentation Mixture | 62.50% |
| Water | 37.50% |
| Total | 100.00% |

Example 3

| Component | Composition (%) by Weight |
| --- | --- |
| Linear Primary Alcohol ($C_{12}$-$C_{15}$) 7 mole Ethoxylate | 22.50% |
| Sodium Lauryl Ether (3 mole) Sulfate (60%) | 7.50% |
| Water | 70.00% |
| Total | 100.00% |

Example 4

| Component | Composition (%) by Weight |
| --- | --- |
| Dioctyl Sulfosuccinate (75%) | 25.00% |
| Hexylene Glycol | 12.50% |
| Water | 62.50% |
| Total | 100.00% |

Example 5

| Component | Composition (%) by Weight |
|---|---|
| Linear Primary Alcohol ($C_{12}$-$C_{15}$) 7 mole Ethoxylate | 22.50% |
| Sodium Lauryl Ether (3 mole) Sulfate (60%) | 7.50% |
| Stabilized Fermentation Mixture (Example 1) | 70.00% |
| Total | 100.00% |

Example 6

| Component | Composition (%) by Weight |
|---|---|
| Dioctyl Sulfosuccinate (75%) | 25.00% |
| Hexylene Glycol | 12.50% |
| Stabilized Fermentation Mixture (Example 2) | 62.50% |
| Total | 100.00% |

The experimental compounds were tested on spinach beginning in the cotyledon stage to 35 days after treatment initiation. A destructive sample of treated plants was taken on days 7, 14, 24, and 35, and root and shoot mass were determined by drying samples and weighing them on a precision balance. At 35 days after treatment initiation, Example 5 and Example 6 promoted statistically greater root mass compared to the untreated control plants, the surfactant only treated plants, and the ferment only treated plants. In addition, fitted lines representing the progression of growth during the trial indicated that Example 5 and Example 6 had significantly greater slopes than all other treatments, which suggests that Example 5 and Example 6 cause greater root mass production than normal growing practices. Shoot mass growth trends suggested that the larger root mass shows absolute higher values of shoot mass in the PSC treatments.

Host Plants:

Spinach, (cv. Avon Hybrid). Two seeds were sown on 7 Jun. 2008 in one-gallon pots (6 inch diameter, approx. 3.8 L volume) filled with UC Mix II (Matkin and Chandler 1957). Soil Mix II is formulated with plaster sand, bark, peat moss, Dolomite, limestone flour, triple super phosphate, potassium nitrate, muriate of potash, ferrous sulfate, copper sulfate, magnesium sulfate, zinc sulfate, and manganese sulfate. Once sown, the pots were watered on a daily basis until the plant were visible above ground. The resulting plants were culled to one plant per pot at the cotyledon (seed leaf) stage. Treatment applications commenced following culling.

Host Plant Care:

Plants were placed on raised greenhouse benches for study. Plants were watered every other day with exactly 50 ml of solution containing fertilizer and 25-ppm of each protein depending on the treatment above. Chemigation (treatment applications and fertilization) will occur simultaneously. The plants were fertilized with Miracle Grow® fertilizer at 100 ppm nitrogen.

Treatment Applications:

Host plant media was fully wetted prior to the start of the trial. Treatment applications were prepared in volume at the appropriate ppm and applied by volumetric cylinder at 50-ml pot to avoid leaching and to maintain consistency in treatment application. Early on, when the plants were small and did not need as many applications, treatments were applied on day 1, 4, 7, 11, and 13 and approximately every third or fourth day thereafter.

| | Treatments | Rate PPM | Frequency |
|---|---|---|---|
| 1. | Example 1 | 25 | During Watering Cycles |
| 2. | Example 2 | 25 | During Watering Cycles |
| 3. | Example 3 | 25 | During Watering Cycles |
| 4. | Example 4 | 25 | During Watering Cycles |
| 5. | Example 5 | 25 | During Watering Cycles |
| 6. | Example 6 | 25 | During Watering Cycles |
| 7. | Untreated Control | Fertilizer only | During Watering Cycles |

Experimental Design:

A randomized complete block design was used in the trial. Five plants per treatment per week were used for sampling, i.e. 5 plants×7 Treatments×5 weeks=175 plants total. Plants treated with selected formulas will be compared to plants treated with water and fertilizer alone.

Sampling:

Three replicates/treatment were removed from the trial prior to the application of selected formulas to compare plants prior to the start of the trial. Thereafter and beginning two weeks after the initial application, five replicates/treatment were removed from the trial at 7, 14, 24, and 35 days to determine if treatments have an effect on plant growth. These plants were photographed to compare plant volumes between treatments. In addition, the plants were dried in an oven, and weighed for dry root and shoot mass on a Jennings Precision 20 brand scale with a 0.002-gram resolution.

Analysis:

Data were analyzed using analysis of variance. Where appropriate, data were transformed log (x+0.5) prior to analysis to satisfy the assumptions of the analysis of variance.

Results and Observations

Root Mass:

Statistical differences between treatments were not observed until Day 35 following initiation of treatment applications (F=9.2; df=6.27; P<0.0001). A significantly greater root mass was observed in plants treated with Example 5 and Example 6 than the Control, 35 days after treatment initiation (Table 2). There appears to be a trend in plants treated with both Example 3 and Example 4 (Surfactants alone) where root mass was beginning to increase but not significantly different than the control. This is most likely due to the ability of the products to wet the soil or other growth media and retain moisture thereby benefiting the plant in the long run. Root mass in plants treated with Example 4 was not significantly different than the Example 5 or Example 6, due to the limited number of plots, but absolute figures show a double the root mass of Example 5 and Example 6 compared to Example 3 and Example 4.

Linear growth trends are as follows. Root mass growth appeared exponential after 30 days of growth under the selected treatments. Example 5 and Example 6 performed best compared to the control and there were no statistical differences in slope between the Control and all other treatments. There is a significant difference between the slopes of the lines of Example 5 and Example 6 and the Control, i.e. there is a significant increase in growth due to the Example 5 and Example 6 compared to the Control.

Shoot Mass:

Statistical differences between treatments were not observed until Day 24 (Table 4. F=2.87; df=6.28; P=0.0262) following initiation of treatment applications and continued on Day 35 (Table 4. F=3.88; df=6.27; P=0.0064). There was a significantly different shoot mass observed in treated plants both 24 and 35 Days after treatment initiation.

Linear growth trends in shoot mass appeared exponential after approximately 30 days of growth under the selected treatments. Linear parameters of shoot mass growth over time are presented in Table 5. It is generally understood that root mass promotes a healthier and larger shoot mass given time to grow, as increase root mass increases the ability of the plant to feed the shoots.

The best examples of the treated plants from each sample date were washed free of potting media and photographed. The progression of root and shoot mass and a comparison of the treatments are presented in the photographs. The surfactants Example 3 and Example 4 acted as soil or media wetting agents, and often a single strand of the roots followed the column of wet soil to the bottom of the pots and proliferated, especially early on in the trial. This is contrasted with an analogous effect with Example 5 and Example 6, the key difference with the PSC compositions being that the root structure was significantly larger throughout the depth of its growth, suggesting an effect more than merely improved wetting of the soil. The larger root mass with the PSC solutions indicated that the combination has a synergistic effect on stimulating the growth of the roots and the subsequent trend toward larger shoot mass. The mechanism has not been studied and is not imperative for the purposes of the current invention, but is it anticipated that the PSC mixtures stimulate symbiotic bacterial activity between roots, bacteria and nutrients bound up organically in the soil. This is important as it suggests that the current invention has fundamental effects that would benefit a broad range of plant species.

There is a trend in the data that is not observed in the statistical analysis that shows that the 'protein only' treatments may have an antagonistic effect, i.e. there was less root and shoot mass in plants treated with ferment only. The lack of positive effects of the protein mixture absent added surfactants is consistent with other work done by the Assignee of the current invention, in that the proteins alone have little practical benefit, but that they multiply the benefits of surfactants when the both ingredients, proteins and surfactants, are formulated together.

It is also important to note that the beneficial effects are seen at very low ppm's compared to previous attempts at using surfactant systems to improve root and plant growth. This provides a major cost benefit and return on investment for the grower.

Further noted was the observation that the Example 5 and Example 6 treated soil maintained a black, "wet" appearance longer than the untreated, and more so than the surfactant only pots. Untreated soil tended to return to a crumby brown appearance more quickly. This is consistent with what would be expected with the other results of the trial. Improved wetting of the soil should improve water retention and be beneficial to root and plant growth.

Finally, it is important to note that the different fermentation and stress shock techniques yielded consistent and positive results. This result indicates that the protein manufacturer has a range of processes to consider vis-à-vis its process and its cost of production.

TABLE 2

Root Mass, gram

| | Control | |
|---|---|---|
| Day | Mean | SE |
| 7 | 0.01 | 0.00 |
| 14 | 0.02 | 0.01 |
| 24 | 0.09 | 0.03 |
| 35 | 1.19 b | 0.22 |

| | Example 5 | | Example 3 | | Example 1 | |
|---|---|---|---|---|---|---|
| Day | Mean | SE | Mean | SE | Mean | SE |
| 7 | 0.02 | 0.01 | 0.02 | 0.00 | 0.01 | 0.00 |
| 14 | 0.01 | 0.00 | 0.01 | 0.00 | 0.02 | 0.00 |
| 24 | 0.21 | 0.07 | 0.17 | 0.05 | 0.05 | 0.02 |
| 35 | 4.61 a | 0.77 | 2.06 b | 0.50 | 1.32 b | 0.32 |

| | Example 6 | | Example 4 | | Example 2 | |
|---|---|---|---|---|---|---|
| Day | Mean | SE | Mean | SE | Mean | SE |
| 7 | 0.03 | 0.01 | 0.03 | 0.01 | 0.02 | 0.00 |
| 14 | 0.02 | 0.01 | 0.01 | 0.00 | 0.02 | 0.01 |
| 24 | 0.16 | 0.04 | 0.16 | 0.05 | 0.27 | 0.06 |
| 35 | 4.34 a | 0.83 | 2.45 ab | 0.40 | 0.58 b | 0.11 |

Shoot Mass, gram

| | Control | |
|---|---|---|
| Day | Mean | SE |
| 7 | 0.01 | 0.00 |
| 14 | 0.03 | 0.01 |
| 24 | 0.27 ab | 0.06 |
| 35 | 1.34 ab | 0.20 |

| | Example 5 | | Example 3 | | Example 1 | |
|---|---|---|---|---|---|---|
| Day | Mean | SE | Mean | SE | Mean | SE |
| 7 | 0.02 | 0.00 | 0.03 | 0.01 | 0.01 | 0.00 |
| 14 | 0.03 | 0.01 | 0.03 | 0.01 | 0.03 | 0.00 |
| 24 | 0.52 a | 0.10 | 0.39 ab | 0.11 | 0.18 b | 0.06 |
| 35 | 1.87 a | 0.29 | 1.49 a | 0.30 | 0.97 ab | 0.19 |

| | Example 6 | | Example 4 | | Example 2 | |
|---|---|---|---|---|---|---|
| Day | Mean | SE | Mean | SE | Mean | SE |
| 7 | 0.02 | 0.01 | 0.02 | 0.00 | 0.02 | 0.00 |
| 14 | 0.02 | 0.01 | 0.03 | 0.01 | 0.05 | 0.01 |
| 24 | 0.46 ab | 0.05 | 0.36 ab | 0.03 | 0.56 a | 0.10 |
| 35 | 1.95 a | 0.34 | 1.19 ab | 0.23 | 0.57 b | 0.11 |

TABLE 4

Line parameters for dry weight root mass in response to selected treatments.
Root Mass, gram

| Treatment | Slope (SE) | RSQ | Y intercept |
|---|---|---|---|
| Control | 0.04 ± 0.01 | 0.60 | (−0.48) ± 0.17 |
| Example 5 | 0.16 ± 0.03 | 0.61 | (−1.91) ± 0.67 |
| Example 6 | 0.15 ± 0.03 | 0.58 | (−1.79) ± 0.66 |
| Equality of Slopes | F = 6.94 | df = 2.54 | P = 0.0021 |

TABLE 5

Line parameters for dry weight shoot mass in response to selected treatments.
Shoot Mass

| Treatment | Slope (SE) | RSQ | Y intercept |
|---|---|---|---|
| Control | 0.05 ± 0.01 | 0.72 | (−0.85) ± 0.19 |
| Example 5 | 0.07 ± 0.01 | 0.74 | (−1.16) ± 0.28 |
| Example 6 | 0.07 ± 0.01 | 0.70 | (−1.26) ± 0.26 |
| Equality of Slopes | F = 1.78 | df = 2.54 | P = 0.1781 |

In a second growth trial of spinach, the treatment methods were the same but the number of pots was increased to ten per data point. Results are shown in Table 6. Again, Day 40 refers to 40 days of treatment, commenced at the cotelydon stage, which was about 14 days after seeding. Day 40 in Table 6 shows a dry root mass five times larger in the PSC treated pots than the control and a shoot mass 2.3 times larger in the PSC treated pots than the control. For the baby, fresh spinach market a typical growth cycle if 50 to 55 days and the results show significant, potential commercial benefits. By Day 60 below the treated pots exhibited a root bound condition and the growth of shoots in the control were able to "catch up" to the treated pots.

TABLE 6

Mean, standard error and N (number of experimental units) of root and shoot dry mass of spinach plants treated with 25 ppm of Example 5.

| | Control | | | PSC | | |
|---|---|---|---|---|---|---|
| | Mean | SE | N | Mean | SE | N |
| Dry Root Mass | | | | | | |
| Day 20 | 0.0 | 0.0 | 9 | 0.1 | 0.0 | 10 |
| Day 40 | 0.4 | 0.1 | 10 | 2.0 | 0.6 | 9 |
| Day 60 | 17.2 | 2.9 | 9 | 42.7 | 8.7 | 7 |
| Dry Shoot Mass | | | | | | |
| Day 20 | 0.1 | 0.0 | 9 | 0.1 | 0.0 | 10 |
| Day 40 | 0.3 | 0.1 | 10 | 0.7 | 0.1 | 9 |
| Day 60 | 18.1 | 2.6 | 9 | 19.9 | 2.0 | 7 |

Plug Growth Data.

Plugs were treated from seeding at 25 ppm Example 5, watered approximately 2 mL per watering with boom sprayer, about every other day in a commercial plug growing facility using production techniques to water and treat plugs. Each data point represents 10 plugs randomly pulled from trays. The PSC had positive effects on root growth on both slow and fast maturing roots. Soil was an organic peat moss blend with wetting agents and nutrients added to the mix.

Ranunculus - analyzed at 10 weeks from seeding

| | average shoots, gr | average root, gr | average dry shoots | average dry roots | Average Height, mm |
|---|---|---|---|---|---|
| Control | 0.294 | 0.263 | 0.040 | 0.0334 | 42.971 |
| Treated | 0.437 | 0.496 | 0.051 | 0.0512 | 59.354 |

Coleus - 5 weeks from seeding

| | average shoots, gr | average roots, gr | average dry shoots | average dry roots |
|---|---|---|---|---|
| Control | 0.622 | 0.410 | 0.0352 | 0.0418 |
| Treated | 0.729 | 0.805 | 0.0462 | 0.0924 |

Petunia - 5 weeks from seeding

| | average shoots, gr | average roots, gr | average dry shoots | average dry roots |
|---|---|---|---|---|
| control | 0.857 | 0.299 | 0.0442 | 0.0229 |
| treated | 0.931 | 0.446 | 0.0484 | 0.052 |

Celosia - 3 weeks from seeding

| | average shoots, gr | average roots, gr | average dry shoots | average dry roots |
|---|---|---|---|---|
| control | 0.281 | 0.1522 | 0.0196 | 0.0166 |
| treated | 0.297 | 0.1972 | 0.0182 | 0.0353 |

Fine Root Hairs and Secondary Roots.

A phenomenon that was not quantified but a significant observation was that the PSC treated plants had a substantially greater amount of fine root hairs and secondary roots than on the untreated control. The phenomena was not observed in surfactant-only or protein-only tests. It was observed in every plant tested, whether treatment was (a) initiated immediately at seeding, (b) initiated at the cotelydon stage as in the spinach trials or (c) initiated in treatment of transplanted, previously untreated plugs. This observation suggests that the root promotion is a fundamental effect that, with proper optimization of treatment protocols, should benefit a wide range of cultivars.

As this relates to PGRs, the PCS treatment is distinctly different in that, (a) it is less specific in terms of when the treatment could be dosed and (b) it is effective in a broad range of plant species. Further, due to a required continuous stimulation of the roots required for benefits to occur, coupled with the fact that the PSC does not bio-accumulate in the environment, is toxic-free (albeit with appropriate surfactant candidates of which there are numerous) and can even be a food product, it poses virtually no risk to the grower, the growers crop or to the environment, even if accidentally misapplied.

Plant Growth Regulator Effects.

It was noted that several species of PSC treated plants exhibited a reduction in shoot height, while at the same time root weights were higher as shown in Tables 7 and 8.

TABLE 7

Tarragon - 8 weeks form seeding

| | average shoots, gr | average roots, gr | average dry shoots | average dry roots | Average Height, mm |
|---|---|---|---|---|---|
| Control | 0.672 | 0.375 | 0.100 | 0.0464 | 54.16 |
| PSC treat | 0.637 | 0.433 | 0.093 | 0.0656 | 41.01 |

TABLE 8

Gerberas - 8 weeks from seeding

|  | average shoots, gr | average roots, gr | average dry shoots | average dry roots | Average Height, Mm |
|---|---|---|---|---|---|
| Control | 2.233 | 0.688 | 0.2274 | 0.072 | 102.219 |
| PSC treat | 2.354 | 1.0838 | 0.246 | 0.119 | 94.12 |

Drip Tape Scale and Fouling Inhibition

In a 3.5 acre field of larkspur flowers, irrigation starts with spraying the field with sprinklers. After the cotyledon stage is achieved, irrigation is done using drip tape. The well water that is used in this field has a high TDS up to 2,000 ppm, always above 1,000 ppm and a relatively high amount of iron, noted by the orange scale color. The high level of solids in the water leads to plugging of holes in the drip tape. This requires laborers to walk the fields and manually dislodge the scaling where water has stopped percolating. Manual cleaning is a costly process. In addition, the life of the tape is limited due to the build-up of scaling with multiple uses.

In our study, half the field was treated as follows and results compared to the control. The dose rate was 1 ppm of PSC formulation Example 5. The irrigation cycle was set for 10 hours once per week, more or less. Total irrigation water used was approximately 1,000,000 gallons at a flow rate of 270 gpm. The drip tape had been previously used and already had some scaling from past use. After 10 weeks of treatment it was noted and photographed from 9 each of 4 foot sections of tape, randomly cut out from both PSC treated and control, that there was significant reduction in scale in the PSC treated as compared the control. It is believed that one of the mechanisms of action of scale formation is biofilm formation that acts as a foundation for scale to form. The detergency properties as well as the uncoupling effects of the PSC, which as shown in previous patent applications of the Assignee are believed to be the basis for keeping the lines clean. In some holes that had already been plugged, the PSC actually cleaned previously plugged holes where percolation of water was observed after a couple weeks of treatment. The benefits provided by the current invention are that, in a drip irrigation system, a multi-purpose function can be achieved. The PSC can keep drip lines clean, while at the same time treating plants, increasing the cost effectiveness of the product due to its multifunctional characteristics.

Foliar Applications

Also disclosed herein are methods of using the above-described PSC such that the proteins improve the function of surfactants, where the protein/surfactant compositions are adjuvants that enhance the performance of plant treatments in above ground application, largely through improved foliar wetting and uptake. Examples of plant treatments utilizing foliar uptake may include, but are not limited to, herbicides and nutrients, with additional foliar applications including fungicides, insecticides and the like. Plant treatment application areas include agricultural, forestry, turf, ornamental, industrial, home, aquatic, and others where such treatments are used. Finally, the use of renewable, naturally derived adjuvant systems, such as the proteins, are desirable because they are environmentally benign with the possibility of being acceptable to being used on food crops certified as "organic."

The improved penetration of agricultural chemical adjuvant systems based on the protein/surfactant systems disclosed herein, and specifically as related to foliar uptake, was a surprise. The waxy surface of many leaves presents a tough barrier for the penetration of plant chemical treatment solutions. The upper leaf surface is coated with a waxy film, the cuticle, which prevents moisture loss and acts as a barrier to insects and chemicals that might harm the plant. A formulation using biologically active compounds (BAC's) and adjuvants ultimately needs to penetrate the plant's cuticle. It has generally been thought that smaller molecules, given the same chemical properties, have a better chance of penetrating the cuticle, or passing through defects in the cuticle, than large ones. The diffusion rate of both lipophilic and hydrophilic compounds across isolated leaf cuticles is thought to be negatively correlated with their molecular weight (MW), or molecular size. That is, lower MW molecules are understood to diffuse through the cuticle and pass through defects in the cuticle more readily than large ones. It was therefore a surprise to have found that the relatively large protein/surfactant complexes, where the proteins are orders of magnitude larger than surfactants, would improve penetration through foliage. Studies of the protein/surfactant mixture indicated that it forms a tight complex that is difficult to break apart, such as when tested by way of dialysis. The proteins themselves are several orders of magnitude larger than surfactant molecules.

Adjuvants, most of which are based on surfactants, are widely used in arable agriculture. They are materials added to spray solutions to improve the performance of BAC's, which are applied to either enhance, inhibit, protect or otherwise affect the growth and development of plants. Examples include compatibility agents (used to aid mixing e.g. two or more pesticides in a common spray solution), drift retardants (used to decrease the potential for pesticide drift), suspension aids (used to mix and suspend pesticide formulations with lower solubility ingredients), spray buffers (used to change the spray solution acidity), and especially surfactants that improve wettability of plant tissues, and enhance absorption and penetration of active ingredients into plant tissues. The biologically active ingredients may directly affect plant metabolism as nutrients, fertilizers, growth regulators, herbicides, fungicides, defoliants, or indirectly, by targeting parasitic, pathogenic, or symbiotic species.

In an example regarding pesticides, it is estimated that in the worldwide use of agricultural chemicals only 0.1% of the total amount of pesticides applied actually reach their targeted destinations where their desired effects are utilized. The remainder is lost to run-off of plants before having a chance to be absorbed, spray drift, off-target spraying, environmental degradation, and the like. Spray drift and targeting of the spray are limited by logistics of the density of plants in a field and mechanical spray systems. An embodiment of the current invention is to reduce the amount of pesticides by improving both the rate of, and degree of, penetration into plants, which would reduce costs and environmental impact of residual pesticides.

The efficiency of a plant's uptake of BAC's, in most cases, determines the optimal dose rates. Improving this efficiency would reduce costs of BAC's, which are in many instances more expensive than the cost of application or the cost of the adjuvants. Many BAC's are cidal agents and are toxic. Minimizing their dose rate would benefit the environment and exposure to farm and nursery laborers. Environmental benefits are gained by reducing dosage rates of micronutrients and fertilizers that can leach as runoff into streams and rivers. In a further embodiment, since phytotoxicity issues of surfactants are related to dosage, a reduced dosage could allow the use of surfactants that would otherwise be phytotoxic at higher dose levels than when formulated with the protein mixture.

Among pesticidal adjuvants, nonylphenol ethoxylates (NPE) surfactants are commercially available and broadly applied due to their low cost and high level of efficacy. However, the wide use of NPE's is currently questioned, because of their slow biodegradation, transfer and bioaccumulation along the food chain and their environmental impacts as endocrine mimickers. Another embodiment of the current invention is the replacement of NPE surfactants and improvement of their performance as pesticidal adjuvants with the protein system of the current invention.

Other approaches to improve on environmental objectives in the chemical treatment of crops include replacing environmentally undesirable synthetic adjuvants with botanically derived, or "green" products that also could meet the requirements of "organic" farming. As an example, U.S. Pat. No. 5,385,750 teaches that polyglycosides are excellent surfactants for solubilizing water-insoluble compounds, but that polyglycosides are poor at wetting and reducing the interfacial tension of solutions and that, "increase in wetting rate and spreading on an oily or waxy surface is important for agricultural pesticide material, which must be spread on the surface of a leaf" The addition of long-chain alcohols, to a certain extent, compensate for the polyglycoside wetting deficiencies. But fatty alcohols have the disadvantages of reducing detergency and having odor problems. Contrary to that, yeast proteins increase surface activity of a variety of synthetic detergents, additionally reduce interfacial tension as compared to those detergents applied alone, without any odor issues, and without creating any environmental or toxicological complications.

Absorption and Contact Angle (Wetting) Measurements

The kinetics of the leaf penetration of an aqueous solution was recorded by measurements of the contact angle of a droplet on the surface of the leaves of two test plants: cabbage and tomato. Cabbage leaves provide a model to show the effectiveness of wetting agents using contact angle, and penetration using absorption measurements, for the genus of waxy leaf plants called brassica and similar ones. Tomato leaves are used as a model to show chemical absorption effects for broadleaf weeds, which includes a large number of invading plant species.

The principle of the method of measuring the contact angle and absorption by the leaf is as follows. A droplet is placed on the surface of the leaf, its evolution is recorded. For each data point, five 1.0 microliter drops of each solution were placed on each type of leaf and allowed to spread and penetrate into the leaf over time. The profile of the drop against the surface of the leaf was recorded and measured optically. The absorption by the leaf is essentially the area of the drop profile at a point in time relative to the area at initial condition. The second measured parameter was the contact angle, i.e. the angle between the leaf surface plane and the tangent to the droplet surface at the crossing point. The contact angle decreased in the course of the exposure, while the droplet spread over the leaf surface. The contact angle is a standard measure of the interfacial tension between the surface and the solution. Surfactants typically facilitate the spread of the liquid on the solid surface, accelerating the decrease in contact angle.

Data in Tables 9 and 10 show that with cabbage leaves, which are especially hydrophobic, creating a high hurdle for any attempt to penetrate the leaves due to their tenacious wax coating, the absorption of protein/surfactant compositions were significantly more pronounced than that of the standard commercial NPE adjuvant. Tomato leaves are more open to water penetration, but there, too, the protein composition was significantly more efficient than the NPE based adjuvant.

Example 7

R-11 (nonylphenol (NPE) based adjuvant)—Commercially available adjuvant from Wilbur-Ellis Company Example 8

| Component | Composition (%) by Weight |
|---|---|
| Dioctyl sulfosuccinate (75%) | 25.00% |
| Hexylene glycol | 12.50% |
| Post-fermentation stress protein mixture | 62.50% |
| Total | 100.00% |

TABLE 9

| Solution | Leaf | Approximate Time to Complete Droplet Penetration (seconds) | Equilibrium Non-penetrated Drop Volume (microliters) | Equilibrium Contact Angle (degrees) |
|---|---|---|---|---|
| Example 7 @ 0.25% | Tomato | 50 | 0.0 | 0° |
| Example 8 @ 0.25% | Tomato | 20 | 0.0 | 0° |
| Example 7 @ 0.25% | Cabbage | 400+ (∞) | 0.4 | 37° |
| Example 8 @ 0.25% | Cabbage | 140 | 0.0 | 0° |

Further comparisons of the protein/surfactant system compared to the surfactant only, indicated that the proteins, when added to the surfactant, accelerated the rate of absorption and the wetting characteristics in both cabbage and tomato leaves, Table 10.

Example 9

| Component | Composition (%) by Weight |
|---|---|
| Dioctyl sulfosuccinate (75%) | 25.00% |
| Hexylene glycol | 12.50% |
| Water | 62.50% |
| Total | 100.00% |

TABLE 10

Rates of sorption into the leaves vary with a general summary being as follows:

| Solution | Leaf | Approximate Time to Complete Droplet Penetration (seconds) | Equilibrium Non-penetrated Drop Volume (microliters) | Equilibrium Contact Angle (degrees) |
|---|---|---|---|---|
| Example 7 @ 0.25% | Tomato | 50 | 0.0 | 0° |
| Example 9 @ 0.25% | Tomato | 30 | 0.0 | 0° |

TABLE 10-continued

Rates of sorption into the leaves vary with a general summary being as follows:

| Solution | Leaf | Approximate Time to Complete Droplet Penetration (seconds) | Equilibrium Non-penetrated Drop Volume (microliters) | Equilibrium Contact Angle (degrees) |
|---|---|---|---|---|
| Example 8 @ 0.25% | Tomato | 20 | 0.0 | 0° |
| Example 7 @ 0.25% | Cabbage | 400+ (∞) | 0.40 | 37° |
| Example 9 @ 0.25% | Cabbage | 400+ (∞) | 0.25 | 22° |
| Example 8 @ 0.25% | Cabbage | 140 | 0.00 | 0° |

In Table 11 a proprietary surfactant that meets label requirements for "organic" farming was evaluated. Organic surfactants have restricted manufacturing processes and typically do not perform as well as non-organic adjuvants in terms of wetting and effectiveness as penetrants. To compensate for some of the difference, higher concentrations are used. In the example of Table 11, the concentration was 1%. As in the case with the NPE based adjuvant, the protein/surfactant system accelerated the penetration, or the absorption, into the cabbage leaf surface compared to the surfactant alone.

Example 10

| Component | Composition (%) by Weight |
|---|---|
| Polyethylene glycol lauryl ether (HLB 10) | 25.00% |
| Water | 75.00% |
| Total | 100.00% |

Example 11

| Component | Composition (%) by Weight |
|---|---|
| Polyethylene glycol lauryl ether (HLB 10) | 25.00% |
| Post-fermentation stress protein mixture | 25.00% |
| Water | 50.00% |
| Total | 100.00% |

Example 12

| Component | Composition (%) by Weight |
|---|---|
| Polyethylene glycol lauryl ether (HLB 10) | 25.00% |
| Post-fermentation stress protein mixture | 75.00% |
| Total | 100.00% |

TABLE 11

| Solution | Leaf | Average Approximate Time to Complete Droplet Penetration (seconds) | Equilibrium Non-penetrated Drop Volume (microliters) | Equilibrium Contact Angle (degrees) |
|---|---|---|---|---|
| Example 10 @ 1% | Cabbage | 400+ (∞) | 0.17 | 18° |
| Example 11 @ 1% | Cabbage | 199 | 0.00 | 0° |
| Example 12 @ 1% | Cabbage | 121 | 0.00 | 0° |

Three additional surfactants were compared to use with and without the addition of proteins. In all cases, the addition of the protein mixture improved the wetting (contact angle) and absorption (penetration) characteristics compared to surfactant alone. The results are shown in Table 12.

Example 13

| Component | Composition (%) by Weight |
|---|---|
| Toximul 8364 Surfactant Proprietary Non-ionic Blend (Stepan) | 10.00% |
| Water | 90.00% |
| Total | 100.00% |

Example 14

| Component | Composition (%) by Weight |
|---|---|
| Toximul 8364 Surfactant Proprietary Non-ionic Blend (Stepan) | 10.00% |
| Post-fermentation stress protein mixture | 20.00% |
| Water | 70.00% |
| Total | 100.00% |

Example 15

| Component | Composition (%) by Weight |
|---|---|
| Agent 3109-6 Surfactant Proprietary Non-ionic Blend (Stepan) | 10.00% |
| Water | 90.00% |
| Total | 100.00% |

Example 16

| Component | Composition (%) by Weight |
|---|---|
| Agent 3109-6 Surfactant Proprietary Non-ionic Blend (Stepan) | 10.00% |
| Post-fermentation stress protein mixture | 20.00% |
| Water | 70.00% |
| Total | 100.00% |

Example 17

| Component | Composition (%) by Weight |
|---|---|
| Agent X-1 Surfactant Proprietary Cationic Blend (Stepan) | 10.00% |
| Water | 90.00% |
| Total | 100.00% |

Example 18

| Component | Composition (%) by Weight |
|---|---|
| Agent X-1 Surfactant Proprietary Cationic Blend (Stepan) | 10.00% |
| Post-fermentation stress protein mixture | 20.00% |
| Water | 70.00% |
| Total | 100.00% |

TABLE 12

A general summary of the results is as follows:

| 80:1 Dilution in Water of | Leaf | Average Approximate Time to Complete Droplet Penetration (seconds) | Equilibrium Non-Penetrated Drop Volume (microliters) | Equilibrium Contact Angle (degrees) |
|---|---|---|---|---|
| Example 13 | Cabbage | 600+ (∞) | 0.49 | 36.6 |
| Example 14 | Cabbage | 600+ (∞) | 0.10 | 12.9 |
| Example 15 | Cabbage | 600+ (∞) | 0.27 | 23.1 |
| Example 16 | Cabbage | 189 | 0.00 | 0.0 |
| Example 17 | Cabbage | 600+ (∞) | 0.15 | 14.8 |
| Example 18 | Cabbage | 141 | 0.00 | 0.0 |

What is claimed is:

1. A method of accelerating root growth in a plant, the method comprising applying to the plant root a composition comprising a) a mixture of proteins and polypeptides, wherein the protein mixture comprises heat shock proteins, and b) a surfactant, whereby root growth is accelerated as compared to an untreated plant;

wherein the mixture of proteins is obtained from aerobic fermentation of yeast, and wherein the fermentation process further comprises subjecting the fermentation mixture to additional heat stress following the fermentation process.

2. The method of claim 1, wherein the yeast is selected from the group consisting of *Saccharomyces cerevisiae, Kluyeromyces maxianus, Kluyeromyces lactus, Candida utilis* (Torula yeast), *Zygosaccaromyces,* and *Pichia* and *Hansanula.*

3. The method of claim 1, wherein the surfactant is non-ionic, anionic, or a combination thereof.

4. The method of claim 1, wherein the growth of fine root hairs and/or the shoot growth of the plant is accelerated.

5. The method of claim 1, wherein the water and nutrient uptake of the plant is accelerated.

6. The method of claim 1, wherein the wetting of growth media is improved.

7. The method of claim 6, wherein the growth media is soil.

8. The method of claim 6, wherein water retention is improved.

9. The method of claim 1, wherein shoot growth is slowed and root growth is enhanced or wherein shoot growth is enhanced once root growth achieves a level of maturity.

10. The method of claim 1, wherein rinsing of salt build-up in soil is improved.

* * * * *